United States Patent [19]

Armstrong

[11] 4,250,051
[45] Feb. 10, 1981

[54] PRESERVATIVE FOR USE IN CALIBRATOR COMPOSITIONS FOR BLOOD ANALYSIS

[75] Inventor: Douglas Armstrong, Coral Springs, Fla.

[73] Assignee: Coulter Electronics, Inc., Hialeah, Fla.

[21] Appl. No.: 972,930

[22] Filed: Dec. 26, 1978

[51] Int. Cl.³ ............................................. G01N 33/16
[52] U.S. Cl. .................................. 252/408; 23/230 B; 424/3; 424/101
[58] Field of Search ..................... 252/408; 23/230 D; 424/3, 101

[56] References Cited

U.S. PATENT DOCUMENTS

| | | | |
|---|---|---|---|
| 3,000,836 | 9/1961 | Ginsburg | 252/408 |
| 3,406,121 | 10/1968 | Jones | 252/408 |
| 3,446,751 | 5/1969 | Weichselbaum | 252/408 |
| 3,519,572 | 7/1970 | Kita | 252/408 |
| 3,558,522 | 1/1971 | Louderback et al. | 252/408 |
| 3,574,137 | 4/1971 | DeCasperis | 252/408 |
| 3,632,735 | 1/1972 | Kita | 252/408 |
| 3,640,896 | 2/1972 | DeCasperis | 252/408 |
| 3,873,467 | 3/1975 | Hunt | 252/408 |
| 3,884,579 | 5/1975 | Mauthner | 252/408 |
| 3,918,905 | 11/1975 | Warren et al. | 252/408 |
| 3,977,995 | 8/1976 | Louderback et al. | 252/408 |
| 4,102,810 | 7/1978 | Armstrong | 252/408 |

OTHER PUBLICATIONS

"The Merck Index", 8th Ed., Merck & Co., Inc., Rahway, N.J., pp. 241-242, pp. 244-245, p. 249 (1968).

*Primary Examiner*—Teddy S. Gron
*Attorney, Agent, or Firm*—Meredith P. Sparks

[57] ABSTRACT

A stable calibrator composition, useful in equipment for determining hematological values in blood samples, comprises a hemolysate of red blood cells which have been lysed with a dilute aqueous solution of saponin to which has been added a halophenol that has a phenol coefficient of between 20 and 90 to provide a concentration from about 1:1000 to about 1:1750 w/v of said halophenol in said hemolysate, said calibrator composition having a pH between 4 and 7. The preferred halophenol is 4-chloro-3,5-xylenol.

4 Claims, No Drawings

PRESERVATIVE FOR USE IN CALIBRATOR COMPOSITIONS FOR BLOOD ANALYSIS

BACKGROUND OF THE INVENTION

This invention concerns the use of a preservative in a hematological reference calibrator composition for instrumentation which determines hematological values in blood samples.

It is common medical diagnostic procedure to analyze and test the blood sample of a patient in order to make certain classic determinations with respect to the blood sample. This procedure is an important aid to the physician. The characteristic parameters to be determined are red blood count (RBC), white blood count (WBC), hematocrit (HCT), hemoglobin (Hgb), mean corpuscular volume (MCH), and mean corpuscular hemoglobin concentration (MCHC). Coulter Electronics, Inc. of Hialeah, Florida and other manufacturers sell several models of blood cell counting and analyzing instruments which are well known in the art. Instruments are sold which will accept a patient's blood sample and process the same sample automatically and continuously to provide one or more of the aforesaid parameters.

The general procedure of such instruments is to add a lysing agent to a suspension of dilute whole blood containing an anticoagulant. The lysing agent destroys the red blood cells and releases their content into solution. This resulting suspension has the coloring matter produced by the broken red cells and the unaffected white cells. A reagent is added to fix the hemoglobin in solution so that the color will be retained and made available for measurement of hemoglobin.

Prior to the use of automated equipment for the purpose of in vitro diagnostic testing of blood samples, calibration of the instrument is required depending on the design and degree of automation of the equipment. A calibrator composition, similar in nature to that of the blood sample which is routinely encountered by the user, is developed which is thoroughly evaluated against the instrument which has been calibrated by reference procedures. This calibrator, which has been provided with an assigned value, is offered to the user in order that he may calibrate his instrument to the assigned value with speed and accuracy.

As to be expected, a hematological composition for use in such a calibrator is prone to bacterial and fungal contamination. Therefore, a suitable preservative agent needs to be added. The typical sterility maintaining substances used in hematology were found to cause side effects, or otherwise not perform suitably for this purpose.

The preservative must be compatible with the blood sample which has been lysed as heretofore mentioned, and the preservative properties of the agent must not be reduced markedly because of the blood protein present. Likewise the antibacterial agent must not form pigments with the blood hemolysate or with other agents to be added later to make the hemoglobin determination. In addition, it must not form a gel which would interfere with keeping the hemolysate in a liquid state for the limited time in which the calibrator is in use, suitably for about 120 days at 4° C.

The preservative must be sufficiently soluble in the hemolysate at the pH resulting from the concentration and amounts of the particular lysing agent used to provide a preservative amount of the agent against bacteria commonly found in the environment, and especially against *Pseudomonas aeruginosa* which is commonly found in the environment.

SUMMARY OF THE INVENTION

According to this invention certain halogen substituted phenolic compounds, hereinafter referred to as "halophenols" have been found useful as antibacterial and antifungal agents for preserving calibrator compositions which have been prepared by lysing whole blood samples with saponin so that these compositions ae useful as calibrators for instruments which determine hematological values in blood samples.

It is known that phenols are effective bacteriocides when used in proper concentrations against pathogens, and that the antibacterial activity is comparatively independent of bacterial concentration and organic matter. In general, the introduction of alkyl groups and of halogen atoms into the phenolic nucleus results in marked increase phenol coefficient. However, it also results in a markedly decreased solubility in aqueous solutions, particularly when the pH is in the range from 4 to 7. Consequently many of the phenols are useful as bacteriocides only in the presence of certain organic solvents, or in alkaline solution as the phenolate salt.

Unexpectedly, it has been found that certain halophenols, which are only very sparingly soluble in distilled water, are several times more soluble in a hemolysate of red blood cells which have been lysed with saponin to have a resultant pH between 4 and 7. For example, although 4-chloro-3,5-xylenol is soluble in distilled water only to the extent of 1:3000 w/v, which amount is insufficient to be effective as a preservative against *Pseudomonas aeruginosa*, the presence of 1% w/v of saponin in the hemolysate increases the solubility to an amount greater than 1:1000 w/v, at which concentration this chlorophenol is known to be effective against common bacteria in the environment, including *Pseudomonas aeruginosa*. See page 76, "Disinfectants, Their Values and Uses", by W. E. Finch, The Macmillan Company, New York, 1953. The preferred concentration of the halophenol in the hemolysate is from about 1:1000 to 1:1750 w/v.

Laboratory findings confirm that 4-chloro-3,5-xylenol dissolves an amount in the order of seven times greater in a 2% saponin solution than in distilled water.

| Solubility of 4-chloro-3,5-xylenol | |
|---|---|
| In distilled water | 31.50 mg/dl |
| In 2% saponin in water | 236.86 mg/dl |

The above results were obtained by ultraviolet scans ($\lambda$ max for 4-chloro-3,5-xylenol at 280 mm) for 1:1000 w/v dilution.

The 4-chloro-3,5-xylenol can be from the Ferro Corporation of Ohio, USA, purchased on the market under the trademark "OTTASEPT®". According to the manufacturer the solubility in water at 25° C. is 0.025 gm/dl. The phenol coefficient is 60.

Examples of other halophenols having a high phenol coefficient which are useful in this invention include 2,4-dichloro-3,5-dimethylphenol (PCMX); 4-bromophenol; 2-chlorophenol; 3-chlorophenol and 4-chloro-3-methylphenol, (PCMC). The phenol coefficient of the individual halophenol is reported in various reference books such as the Merck Index, 9th Edition (1976), or can be determined by methods well known in the art. A phenol coefficient between 20 and 90 is preferred.

Saponin is a natural product contained in the roots of some plants which forms a lather in aqueous solutions. Chemically, each saponin consists of a sapongenin which may be a steroid or a triterpene, and a sugar which may be glucose, galactose, pentose, or methylpentose. It can be purchased from several supply houses. The saponin recommended for use in this invention is the commercial product having a high degree of hemolytic quality. Saponin is added in a concentration of 0.5 to 3% w/v of the final product. When it is used as a lysing agent for the red blood cells in whole blood, the resultant solution has a pH between 4 and 7.

Without being restricted by any theory of action, although the bacteriocidal activity of halophenols has long been known, the poor solubility of these compounds in neutral or slightly acid solution has restricted their use as a preservative to those circumstances where the presence of an organic solvent or alkali pH is unobjectionable. The present discovery is that the conjoint use of a saponin and a halophenol will increase the solubility of the halophenol to an amount in which it acts as an effective preservative in calibrator compositions for apparatus which determine hematological values in blood samples.

For procedures and equipment which include a white cell count, the aldehyde fixed red cells (human, animal, fowl, or reptile) which resubstitute for the white cells, platelets or red blood cells found in the usual blood samples are added to the hemolysate containing the preservative to give a suitable calibrator for hematological analysis.

DESCRIPTION OF A PREFERRED PROCEDURE

The following detailed procedure describes a method for preparation of a calibrator composition for determining hematological values which include both the white blood cell count (WBC) and the hemoglobin (Hgb) determination. However, it is to be understood that this invention is not limited to this exact procedure which is included for purposes of illustration and not of limitation. The calibrator of this invention can be used for apparatus which makes a determination of either or both the white blood cells (WBC) and the hemoglobin (Hgb), and can also be used in apparatus which makes either one or both of these determinations in combination with or in addition to other blood cell parameter measurements.

1. Units of fresh, three-times washed with sterile saline solution (0.9% w/v sodium chloride in distilled water), packed red cells are prepared as a pool to give a volume in excess of that volume required for the batch size of the finished product.

2. After thorough mixing, for example, by rolling the closed bottle at 8 to 12 revolutions per minute for a period of 15 to 30 minutes, a sample is removed and the hemoglobin level determined. From the determined hemoglobin level, the volume of packed red blood cells required to give the desired product hemoglobin level is calculated.

3. The required volume of packed cells is then measured out into another sterile bottle volume required for end product batch.

4. To the packed cells is added a calculated volume of a filtered 2% w/v aqueous solution of saponin solution prepared with sterile distilled water to bring the hemoglobin to its desired value. For this purpose a commercial grade of saponin is filtered through a filter membrane of $1.2\mu$ pore size. The final concentration of saponin in the hemolysate is about 1% w/v.

5. The bottle is then closed and inverted several times. Lysis of the red blood cells is seen by the deep red ink appearance of the solution.

6. 4-Chloro-3,5-xylenol powder is then added to the hemolysate at a rate of 0.1 gm per dl of the final product batch volume.

7. The bottle is closed, inverted several times, and then placed on a mechanical roller mixer for about two to three hours. After the solution has been thoroughly mixed, a calculated volume of formaldehyde-fixed red blood cells is added to the solution. The calculation volume of fixed red blood cells will depend on the desired white blood cell particle count in the end product.

8. After adding the formaldehyde-fixed red blood cells, the blood is closed and placed on the mechanical roller mixer for about thirty minutes. When the solution has been thoroughly mixed, a sample is taken for the white blood count and hemoglobin determination, using the instrument model on which the calibrator is to be used.

9. If the white blood count and/or hemoglobin are out of the range of expected values, the values can be adjusted by adding more packed red blood cells, or saponin solution or fixed cells, whatever the case may be.

10. Once a batch of the calibrator has been prepared or completed, it can be used immediately for filling small vials which are then stored at a cool temperature such as 4° C. In the alternative the large bottle is placed in storage at a cool temperature such as 4° C. until required for filling. Before filling into vials, the solution is allowed to warm to about 72° C. and rolled until thorough mixing results.

11. When the calibrator material has been filled into the appropriate vials, a statistically-valid sampling is taken of the vials for determination of the "CALIBRATOR: CALIBRATION VALUE".

12 The "CALIBRATOR:CALIBRATION VALUES" are obtained by running all of the sample vials on the instrument or instrument system on which it is intended to be used. The instrument or instrument system has been previously calibrated using a fresh normal blood sample. The hemoglobin and white cell count of the fresh normal blood sample have been determined by recognized reference procedures. Once the "CALIBRATOR:CALIBRATION VALUES" have been determined and statistically analyzed, the final "CALIBRATION VALUES" are assigned for the use's use in calibrating his own instruments or instrument.

While the above procedure has been developed particularly for use in equipment operating under the Coulter principle, the calibrator compositions of this invention can be used in other hemoglobin methodologies and particle counting systems, if prior reference values have been obtained for the calibrator composition with the alternate methodology or system as in the case of this calibrator, and this is true irrespective of the lysing agent or the hemoglobin reagent used in the alternate methodology. For example, the lysing agent in the alternate system can contain a quaternary ammonium alkyl salt which is not saponin, and the hemoglobin can be determined as carbonyl or oxyhemoglobin instead of cyanmethemoglobin.

It is anticipated that those skilled in the art will find it advantageous to introduce certain technical changes to suit particular testing and measuring need, while at the same time remaining within the scope of the invention.

I claim:

1. A stable calibrator composition, useful for calibrating instruments which determine hematological values in whole blood samples, comprising a mixture of
   (a) a hemolysate of red blood cells which have been lysed with an aqueous solution of saponin, and
   (b) a preservative amount of 4-chloro-3,5-xylenol, the concentration of said 4-chloro-3,5-xylenol in said hemolysate being from about 1:1000 to 1:1750 w/v, and said hemolysate having a pH between 4 and 7.

2. The composition according to claim 1 to which is added a calculated amount of aldehyde fixed red blood cells, sufficient to substitute for the white blood cells which are normally found in whole blood.

3. A process for the preparation of a stable composition useful for calibrating instruments which determine hematological values including white cell count in blood samples which comprises the steps of:
   (a) lysing the red blood cells by agitating with an aqueous solution of saponin to form a hemolysate having a pH between 4 and 7; and
   (b) adding to said hemolysate a preservative amount of 4-chloro-3,5-xylenol, the concentration of said 4-chloro-3,5-xylenol in said hemolysate being from about 1:1000 to 1:1750 w/v.

4. The method of claim 3 wherein a calculated amount of aldehyde fixed red blood cells, sufficient to substitute for the white blood cells which are normally found in whole blood is added to said hemolysate in step (b).

* * * * *

UNITED STATES PATENT AND TRADEMARK OFFICE
CERTIFICATE OF CORRECTION

PATENT NO. : 4,250,051

DATED : February 10, 1981

INVENTOR(S) : Douglas Armstrong

It is certified that error appears in the above—identified patent and that said Letters Patent is hereby corrected as shown below:

Column 2, line 12, change "ae" to --are--; column 4, line 20, change "blood" to --bottle--; column 4, line 53, change "use's" to --user's--.

Signed and Sealed this

Seventeenth Day of August 1982

[SEAL]

Attest:

Attesting Officer

GERALD J. MOSSINGHOFF

Commissioner of Patents and Trademarks